(12) United States Patent
Hosseini et al.

(10) Patent No.: US 8,778,999 B2
(45) Date of Patent: Jul. 15, 2014

(54) NON-STEROIDAL ANTI-INFLAMMATORY OPHTHALMIC COMPOSITIONS

(75) Inventors: Kamran Hosseini, Los Altos, CA (US);
Lyle Bowman, Pleasanton, CA (US);
Erwin C. Si, Alameda, CA (US);
Stephen Pham, Sacramento, CA (US)

(73) Assignee: Insite Vision Incorporated, Alameda, CA (US)

( * ) Notice: Subject to any disclaimer, the term of this patent is extended or adjusted under 35 U.S.C. 154(b) by 155 days.

(21) Appl. No.: 12/398,657

(22) Filed: Mar. 5, 2009

(65) Prior Publication Data

US 2010/0227928 A1     Sep. 9, 2010

(51) Int. Cl.
| | |
|---|---|
| A61K 31/196 | (2006.01) |
| A61K 31/192 | (2006.01) |
| A61K 9/00 | (2006.01) |
| A61K 45/06 | (2006.01) |
| A61K 47/32 | (2006.01) |
| A61K 47/34 | (2006.01) |

(52) U.S. Cl.
CPC .............. *A61K 31/192* (2013.01); *A61K 47/34* (2013.01); *A61K 9/0048* (2013.01); *A61K 45/06* (2013.01); *A61K 47/32* (2013.01)
USPC ........... 514/567; 514/561; 514/557; 514/553; 424/427; 424/78.02

(58) Field of Classification Search
None
See application file for complete search history.

(56) References Cited

U.S. PATENT DOCUMENTS

| | | |
|---|---|---|
| 2,798,053 A | 7/1957 | Brown |
| 4,136,250 A | 1/1979 | Mueller et al. |
| 4,192,827 A | 3/1980 | Mueller et al. |
| 4,548,990 A | 10/1985 | Mueller et al. |
| 4,910,225 A | 3/1990 | Ogawa et al. |
| 5,192,535 A | 3/1993 | Davis et al. |
| 5,221,696 A * | 6/1993 | Ke et al. ................. 514/786 |
| 5,332,582 A | 7/1994 | Babcock et al. |
| 5,558,876 A | 9/1996 | Desai et al. |
| 6,060,463 A * | 5/2000 | Freeman ................. 514/81 |
| 8,129,431 B2 | 3/2012 | Sawa et al. |
| 2003/0077302 A1* | 4/2003 | Claus-Herz et al. ....... 424/400 |
| 2003/0143259 A1* | 7/2003 | Roy et al. ................. 424/427 |
| 2005/0113311 A1* | 5/2005 | Robledo ................. 514/19 |
| 2006/0171984 A1* | 8/2006 | Cromack et al. ......... 424/423 |
| 2006/0183698 A1 | 8/2006 | Abelson |
| 2007/0254841 A1 | 11/2007 | Ousler et al. |

(Continued)

FOREIGN PATENT DOCUMENTS

| | | |
|---|---|---|
| EP | 1586316 A1 | 10/2005 |
| WO | 2008153746 A1 | 12/2008 |

OTHER PUBLICATIONS

"Comparison of cyclooxygenase inhibitory activity and ocular anti-inflammatory effects of ketorolac tromethamine and bromfenac sodium" by Waterbury et al., Curr. Med. Res. Opin. 22, 1133-40 (2006).*

(Continued)

*Primary Examiner* — Wu-Cheng Winston Shen
*Assistant Examiner* — Theodore R West
(74) *Attorney, Agent, or Firm* — McDermott Will & Emery LLP

(57) ABSTRACT

The disclosure provides compositions and systems for topical ophthalmic application, which include an aqueous mixture of bromfenac and flowable mucoadhesive polymer, for treating inflammation and inflammatory conditions of the eye.

21 Claims, 1 Drawing Sheet

(56) References Cited

U.S. PATENT DOCUMENTS

| | | | |
|---|---|---|---|
| 2007/0265341 A1* | 11/2007 | Dana et al. | 514/560 |
| 2007/0287749 A1* | 12/2007 | Sawa et al. | 514/567 |
| 2008/0039398 A1* | 2/2008 | Ousler et al. | 514/12 |
| 2008/0070908 A1* | 3/2008 | Muller et al. | 514/230.2 |
| 2013/0096199 A1 | 4/2013 | Padilla et al. | |

OTHER PUBLICATIONS

"Stability study of azithromycin in ophthalmic preparations" by Moreno et al., Brazilian J. Pharma. Sci. 45, 219-26 (2009).*

"Topical Ocular Delivery of NSAIDs" by Ahuja et al., AAPS Journal 10, 229-41 (2008).*

"Ocular Surface Distribution and Pharmacokinetics of a Novel Ophthalmic 1% Azithromycin Formulation" by Akpek et al., J. Ocular Pharmacol. Therap. 25, 433-39 (2009).*

Shulman et al., "Comparative evaluation of the short-term bactericidal potential of a steroid-antibiotic combination versus steroid in the treatment of chronic bacterial blepharitis and conjunctivitis," European Journal of Ophthalmology, vol. 6, No. 4, (1996) pp. 361-367.

Wagh, V. D. et al., "Formulation and evaluation of ophthalmic insert drug delivery system of forskolin," Asian Journal of Pharmaceutics, Oct.-Dec. 2008, pp. 221-224.

Saettone et al., "Evaluation of muco-adhesive properties and in vivo activity of ophthalmic vehicles based on hyaluronic acid," International Journal of Pharmaceutics, vol. 51, No. 3 (May 1, 1989) pp. 203-212.

Bucci. Jr, F.A. et al., "Comparison of ketorolac 0.4% and bromfenac 0.09% at trough dosing: Aqueous drug absorption and prostaglandin E2 levels," J Cataract Refract Surg, vol. 34, Sep. 2008, pp. 1509-1512.

Baklayan et al., :24-Hour Evaluation of the Ocular Distribution of 14C-Labeled Bromfenac Following Topical Instillation into the Eyes of New Zealand White Rabbits, Journal of Ocular Pharmacology and Therapeutics, vol. 24, No. 4, 2008, pp. 392-398.

Supplementary European Search Report EP Application No. 10749380.1 dated Aug. 20, 2013.

European Search Report issued in Application No. 10749380.1-1460 dated Aug. 20, 2013.

Prolensa™ Package Insert, Bausch & Lomb Incorporated.

Prolensa™ Orange Book Listing.

Bromday™ Package Insert, ISTA Pharmaceuticals, Inc., 2010.

* cited by examiner

Aqueous Humor Bromfenac Concentrations Following a Single Dose Application
A
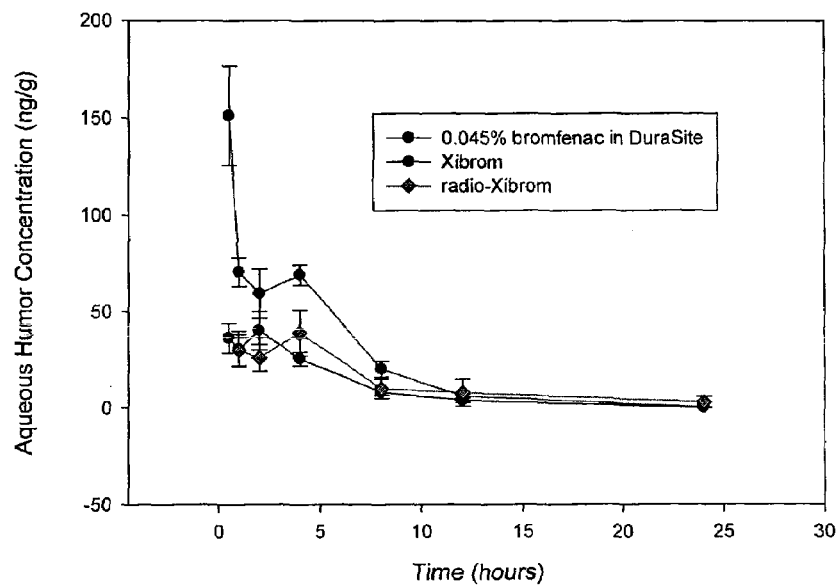
Aqueous Humor Bromfenac Concentrations Following a Single Dose Application
B
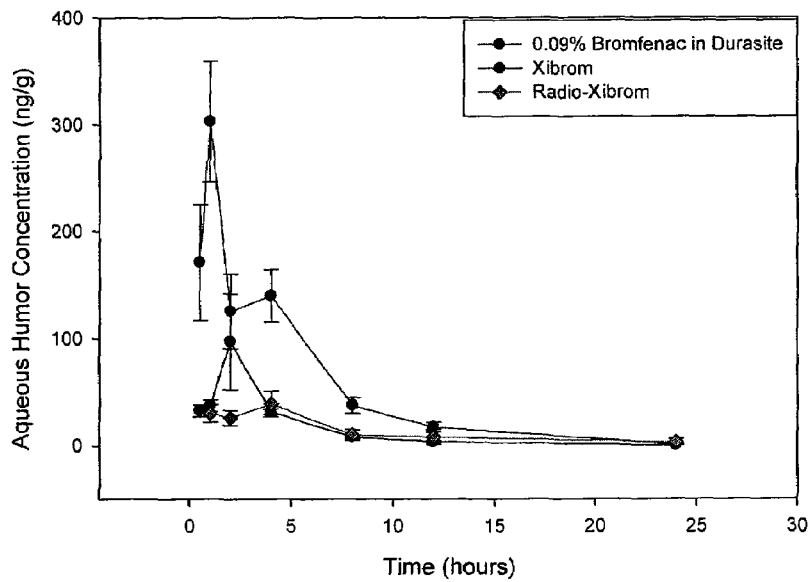

NON-STEROIDAL ANTI-INFLAMMATORY OPHTHALMIC COMPOSITIONS

FIELD OF THE INVENTION

The present invention relates to ophthalmic formulations; more particularly to ophthalmic formulations of nonsteroidal anti-inflammatory agents; more particularly the present invention relates to ophthalmic formulations of bromfenac.

BACKGROUND OF THE INVENTION

In topical administration of medicaments to the eye, a variety of factors can be important, among them: comfort, control, consistency and accuracy of dosage, type and time of any vision interference, ease of administration, and timing of delivery. Prior ophthalmic delivery systems for bromfenac have suffered drawbacks in one or more of those areas.

SUMMARY OF THE INVENTION

It is an object of the invention to provide a novel composition of bromfenac that can overcome any of the above drawbacks.

The present invention provides topical ophthalmic formulations containing a non-steroidal anti-inflammatory agent, bromfenac, and a flowable mucoadhesive polymer. It has been discovered that the composition of the invention not only facilitates a slow release of bromfenac over a long period of time, but also unexpectedly facilitates a high absorption and retention of bromfenac by the aqueous humor of the eye as compared with other bromfenac formulations currently available on the market.

In one aspect, the present invention relates to an ophthalmic composition including a flowable mucoadhesive polymer and a therapeutically effective amount of bromfenac, wherein the composition has a viscosity formulated for administration to the eye of a mammal in drop form. In another related embodiment, bromfenac is retained in or carried with the flowable mucoadhesive polymer. In another related embodiment, the flowable mucoadhesive polymer is a sustained release delivery system. In another related embodiment, the flowable mucoadhesive polymer is a carboxy-containing polymer, such as polycarbophil or DuraSite®. In another embodiment, the ophthalmic composition further includes a therapeutically effective amount of ketorolac. In another related embodiment, the mucoadhesive polymer is in an amount of about 0.5% to about 1.5% by weight of the composition. In another related embodiment, the polymer is in an amount of about 0.8% to about 1.0% by weight of the composition. In another related embodiment, bromfenac is in an amount of about 0.005% to about 0.5% by weight of the composition. In another related embodiment, bromfenac is in an amount of about 0.01% to about 0.2% by weight of the composition. In another related embodiment, the bromfenac in an amount of about 0.045% to about 0.09% by weight of the composition. In another related embodiment, the composition has a pH of about 7.4 to about 8.5. In another related embodiment, the composition has a pH of about 8.3. In another related embodiment, the viscosity of the composition is in the range of about 1,000 to about 2,000 centipoises (cps). In another related embodiment, the viscosity of the composition is about 1,500 cps.

In another aspect, the invention relates to a sustained release bromfenac delivery system, including a flowable mucoadhesive polymer and a therapeutically effective amount of bromfenac in an ophthalmic composition; wherein the flowable mucoadhesive polymer is in an amount of about 0.5% to about 1.5% by weight of the composition and the bromfenac is in an amount of about 0.005% to about 0.5% by weight of the composition. In another related embodiment, bromfenac is in an amount of about 0.01% to about 0.2% by weight of the composition. In another related embodiment, the bromfenac in an amount of about 0.045% to about 0.09% by weight of the composition. In a related embodiment, the bromfenac is retained in or carried with the flowable mucoadhesive polymer. In another related embodiment, the flowable mucoadhesive polymer is a carboxy-containing polymer. In another related embodiment, the carboxy-containing polymer is polycarbophil or DuraSite®. In another related embodiment, the bromfenac is in an amount of about 0.01% to about 0.09% by weight of the composition. In another related embodiment, the polymer is in an amount of about 0.8% to about 1.0% by weight of the composition. In another related embodiment, the composition has a pH of about 7.4 to about 8.5. In another related embodiment, the composition has a pH of about 8.3. In another related embodiment, the viscosity of the composition is in the range of about 1,000 to about 2,000 cps. In another related embodiment, the viscosity of the composition is about 1,500 cps.

In another aspect, the invention relates to a process for therapeutic treatment of the eye of a mammal including: (a) providing an ophthalmic composition having bromfenac in a therapeutically effective amount of about 0.005% to about 0.5% by weight of the composition and a flowable mucoadhesive polymer in an amount of about 0.5% to about 1.5% by weight of the composition; (b) administering said composition to the eye of a mammal in need thereof to treat inflammation or inflammatory conditions of the eye. In another related embodiment, the bromfenac is retained in or carried with the flowable mucoadhesive polymer. In another related embodiment, the flowable mucoadhesive polymer is a carboxy-containing polymer. In another related embodiment, the carboxy-containing polymer is polycarbophil or DuraSite®. In another related embodiment, bromfenac is in an amount of about 0.01% to about 0.2% by weight of the composition. In another related embodiment, the bromfenac in an amount of about 0.01% to about 0.09% by weight of the composition. In another related embodiment, the bromfenac in an amount of about 0.045% to about 0.09% by weight of the composition. In another related embodiment, the polymer is in an amount of about 0.8% to about 1.0% by weight of the composition. In another related embodiment, the composition has a pH of about 7.4 to about 8.5. In another related embodiment, the composition has a pH of about 8.3. In another related embodiment, the viscosity of the composition is in the range of about 1,000 to about 2,000 cps. In another related embodiment, the viscosity of the composition is about 1,500 cps.

In another aspect, the invention relates to a composition or method for combination therapy of the eye of a mammal including: an ophthalmic composition having a therapeutically effective amount of bromfenac, a therapeutically effective amount of ketorolac and a flowable mucoadhesive polymer such as DuraSite®, wherein the composition has a viscosity formulated for administration to the eye of a mammal in drop form. In another aspect, the invention relates to a composition or method for combination therapy of the eye of a mammal including: an ophthalmic composition having a therapeutically effective amount of bromfenac, a flowable mucoadhesive polymer such as DuraSite® and one or more additional non-steroidal anti-inflammatory agent such as, for example, a therapeutically effective amount of ketorolac. In an embodiment, ketorolac is included in the composition of the invention in an amount of about 0.01% to about 1% by weight of the composition. In another embodiment, ketorolac is included in the composition of the invention in an amount of about 0.4% to about 0.5% by weight of the composition. In another aspect, the invention relates to a composition or method for combination therapy of the eye of a mammal including: an ophthalmic composition having a therapeutically effective amount of bromfenac, a flowable mucoadhesive polymer such as DuraSite® and one or more steroidal anti-inflammatory agent. In another aspect, the invention relates to a composition or method for combination therapy of the eye of a mammal including: an ophthalmic composition having a therapeutically effective amount of bromfenac, a flowable mucoadhesive polymer such as DuraSite® and one or more antibacterial agent. In an embodiment, relating to any of the above aspects, the invention relates to a composition or method for combination therapy of the eye of a mammal including: an ophthalmic composition having a therapeutically effective amount of bromfenac, a flowable mucoadhesive polymer such as DuraSite® and an additional therapeutically active agent selected from the group consisting of antibacterial antibiotic agent, synthetic antibacterial agent, antifungal antibiotic agent, synthetic antifungal agent, antineoplastic agent, steroidal anti-inflammatory agent, non-steroidal anti-inflammatory agent, anti-allergic agent, glaucoma-treating agent, antiviral agent and anti-mycotic agent.

It is to be understood that both the foregoing general description and the following detailed description are exemplary and explanatory only and are not restrictive of the invention, as claimed.

BRIEF DESCRIPTION OF THE DRAWINGS

FIG. 1A shows the differences in aqueous humor concentration of bromfenac as a factor of time following a single dose application of 0.045% bromfenac in DuraSite®, Xibrom® and radioactively labeled bromfenac (radio-Xibrom®) to the eye of a mammal at time zero.

FIG. 1B shows the differences in aqueous humor concentration of bromfenac as a factor of time following a single dose application of 0.09% bromfenac in DuraSite®, Xibrom® and radioactively labeled bromfenac (radio-Xibrom®) to the eye of a mammal at time zero.

DETAILED DESCRIPTION OF THE INVENTION

The present invention generally relates to topical ophthalmic formulations containing bromfenac, a non-steroidal anti-inflammatory agent (NSAID), and a flowable mucoadhesive polymer. Not only have the applicants found that the compositions of the invention facilitate a slow release of bromfenac over a longer period of time, but they have also unexpectedly discovered that the compositions of the invention facilitate a higher absorption and retention of bromfenac by the aqueous humor of the eye as compared to other bromfenac formulations.

The increased absorption and retention of bromfenac in the eye, provided by the compositions of the present invention, allow subjects to apply fewer doses (e.g., once per day) of bromfenac to treat the affected eye. Reduced dosing increases convenience of using the bromfenac formulation, while a higher absorption and retention of bromfenac in the eye increases the efficacy of bromfenac in treating inflammation and inflammatory conditions of the eye. In general, it has been shown that control over dosing and concentration of NSAIDs delivered to the aqueous humor has been correlated to a higher efficacy in treating inflammation of the eye (Bucci et al., J Cataract Refract Surg. 34(9):1509-12 (2008)).

Non-steroidal anti-inflammatory agents are known to inhibit cyclooxygenases, enzymes associated with pain and inflammation in mammals. Cyclooxygenases are essential in the biosynthesis of prostaglandins, which have been shown in many animal models to be mediators of intraocular inflammation. Although steroidal compounds have been used to treat such inflammation, non-steroidal anti-inflammatory agents from the group of drugs known as cyclooxygenase inhibitors have been substituted for steroids because they have not shown the same propensity to produce side-effects in ocular tissues as compared to ophthalmic steroids. Non-steroidal agents are also widely prescribed to reduce pain and inflammation in a wide number of tissues. When used as topical agents in the eye, they suppress inflammatory responses and have been shown to prevent particular side-effects of surgical trauma (on the pupil preventing surgical meiosis), fluid accumulating in the back of the eye after cataract surgery (post-surgical macular edema) and the appearance of inflammatory cells and vessel leakage in the anterior chamber. Topical application of non-steroidal anti-inflammatory agents in the eye also appears to relieve some of the itching due to allergic conjunctivitis. Diclofenac sodium, suprofen, and flurbiprofin are non-steroidal anti-inflammatory agents that have been used for the treatment of postoperative inflammation in patients who have undergone cataract extraction.

Bromfenac is a non-steroidal anti-inflammatory agent commonly used to treat patients who have undergone cataract removal. The chemical structure of bromfenac is disclosed in U.S. Pat. No. 4,910,225, which is hereby incorporated in its entirety by reference. A sterile ophthalmic solution of bromfenac as sodium salt equivalent to 0.09% bromfenac free acid is currently marketed as Xibrom® by ISTA/Senju Pharmaceuticals with a recommended dosing schedule of 1 drop per 12 hours. However, Xibrom® has been shown not to provide a good control of prostaglandin-mediated inflammation when compared to ketorolac (another NSAID) partly due to its concentration drop in the eye after twelve hours, consistent with its on-label dosing schedule (Bucci et al., J Cataract Refract Surg. 34(9):1509-12 (2008)).

It is an object of the invention to provide novel topical ophthalmic formulations containing bromfenac and a flowable mucoadhesive polymer that reduce the required dosing of bromfenac to, for example, once per day administration while facilitating the absorption and retention of a higher concentration of bromfenac in the eye and/or its related or surrounding tissues such as, for example, retina to treat prostaglandin-mediated inflammation or inflammatory conditions of the eye.

As used herein the term "ophthalmic composition" refers to a composition intended for application to the eye or its related or surrounding tissues such as, for example, eyelid. The term also includes compositions intended to therapeutically treat conditions of the eye itself or the tissues surrounding the eye and compositions administered via the ophthalmic route to treat therapeutically a local condition other than that involving the eye. The ophthalmic composition can be applied topically or by other techniques, known to persons skilled in the art, such as injection to the eye or its related tissues. Examples of suitable topical administration to the eye include administration in eye drops and by spray formulations. A further suitable topical administration route is by subconjunctival injection. The agents can also be provided to the eye periocularly or retro-orbitally. Although it is an advantage of the invention that intracameral administration is not required, this and other routes of administration are not outside the scope of the invention.

As used herein the term "flowable mucoadhesive polymer" refers to a carboxy-containing polymer, e.g., lightly crosslinked polymers of acrylic acid or the like, having an optimal in vivo mucosal absorption rate, safety, degradability and flowability for an eye drop. The flowable mucoadhesive polymers used in the present invention are water insoluble, water-swellable, biodegradable polymer carriers including lightly crosslinked carboxy-containing polymers such as polycarbophil (Noveon® AA-1, Lubizol Corp., Wickliffe, Ohio) or other Carbopol® polymers (Lubizol Corp., Wickliffe, Ohio). Suitable carboxy-containing polymers for use in the present invention and methods for making them are described in U.S. Pat. No. 5,192,535 to Davis et al. which is hereby incorporated in its entirety by reference. A suitable carboxy-containing polymer system for use in the present invention is known by the tradename DuraSite® (InSite Vision Inc., Alameda, Calif.), containing polycarbophil, which is a sustained release topical ophthalmic delivery system that releases drug at a controlled rate. DuraSite® encompass lightly crosslinked polymers that are prepared by suspension or emulsion polymerizing at least about 90% by weight of a carboxyl-containing monoethylenically unsaturated monomer such as acrylic acid with from about 0.1% to about 5% by weight of a polyfunctional, or difunctional, crosslinking agent such as divinyl glycol (3,4-dihydroxy-1, 5-hexadiene), having a particle size of not more than about 50 µm in equivalent spherical diameter, when formulated with an ophthalmic medicament, e.g., bromfenac, into solutions or suspensions in aqueous medium in which the amount of polymer ranges from about 0.5% to about 1.5% by weight, based on the total weight of the aqueous suspension, the pH is from about 7.4 to about 8.5, and the osmotic pressure (osmolality or tonicity) is from about 10 mOsM to about 400 mOsM, provide new topical ophthalmic medicament delivery systems having suitably low viscosities which permit them to be easily administered to the eye in drop form, and hence be comfortably administrable in consistent, accurate dosages. The compositions of the invention containing DuraSite® will rapidly gel in the eye after coming into contact with the eye's tear fluid to a substantially greater viscosity than that of the originally-introduced suspension or solution and thus remain in place for prolonged periods of time to provide sustained release of the ophthalmic medicament.

As used herein the term "retained in or carried with" or "retaining or carrying" embraces generally all ways that bromfenac can be associated with the flowable mucoadhesive polymer. For example, bromfenac can be in aqueous solution dispersed throughout the polymer. A bromfenac concentration of up to about 0.09% will be in solution mixed with or dispersed throughout the flowable mucoadhesive polymer carrier. Bromfenac can also be in suspension with the polymer depending on its concentration. For example, when bromfenac is used in an amount more than about 0.36% by weight of the composition, some of the bromfenac can be in suspension with the polymer carrier while an amount of up to about 0.36% of bromfenac will still be in solution and mixed with the polymer carrier.

As used herein the term "inflammation or inflammatory conditions of the eye" refers to an ocular disease or any inflammatory condition of the eye and external tissues surrounding eye, e.g., eyelid, influenced by various exogenous or endogenous agents or events. Endogenous factors include, but are not limited to, inflammatory chemokines, cytokines, mediators, nuclear transcription factors, antigens, autogens or hormones that can cause acute or chronic inflammation, pain, redness, swelling, wateriness and itchiness of the eye or its surrounding tissues. Exogenous agents or events include, but are not limited to, infection, injury, radiation, surgery or damage to the eye or its surrounding tissues, which initiate biochemical reactions leading to an inflammation. An ocular disease is one caused by vascular leakage in the eye or by inflammation in the eye. Examples of conditions related to inflammation in the eye include, but are not limited to the following: surgical trauma; dry eye; allergic conjunctivitis; viral conjunctivitis; bacterial conjunctivitis; blepharitis; anterior uveitis; injury from a chemical; radiation or thermal burn; or penetration of a foreign body, signs and symptoms of eye problems (e.g., pain in or around the eye, redness especially accompanied by pain in the eye (with or without movement), extreme light sensitivity, halos (colored circles or halos around lights), bulging (protrusion) of the eye or swelling of eye tissues, discharge, crusting or excessive tearing; eyelids stuck together, especially upon awakening, blood inside the front of the eye (on the colored part) or white of the eye); cataracts; pain and inflammation associated with wearing contact lenses; corneal conditions (e.g., conjunctival tumor excision, conjunctivitis ("Pink Eye"), cornea edema after cataract surgery, corneal clouding, corneal transplantation, corneal ulcer, dry eye syndrome, dystrophies, conditions associated with excimer laser phototherapeutic keratectomy, herpes simplex keratitis, keratoconus, pterygium, recurrent erosion syndrome); eye movement disorders; glaucoma; ocular oncology, oculoplastics (e.g., cosmetic surgery, enucleation, eyelid and orbit injuries, ectropion, entropion, graves' disease, involuntary eyelid blinking); conditions associated with refractive surgery; and retinal conditions.

As used herein the term "sustained release delivery system" or "sustained release composition" refers to a composition comprising a flowable mucoadhesive polymer—which is a carboxy-containing polymer such as polycarbophil and DuraSite®, as described in U.S. Pat. No. 5,192,535—which facilitates a sustained release of bromfenac. Such compositions may include other biologically active agents besides bromfenac. Typically, the sustained release compositions of the invention can contain from about 0.005% (w/w) to about 0.5% of bromfenac (free acid). In an embodiment, the range of bromfenac loading is between about 0.01% (w/w) to about 0.2%. In another embodiment, the range of bromfenac loading is between about 0.045% (w/w) to about 0.09%. The sustained release delivery systems or compositions of this invention can be formed into many shapes such as a solution, a gel, a film, a pellet, a rod, a filament, a cylinder, a disc, a wafer, nanoparticles or a microparticle. A "microparticle" as defined herein, comprises a blend polymer component having a diameter of less than about one millimeter and having bromfenac dispersed therein. A microparticle can have a spherical, non-spherical or irregular shape. Typically, the microparticle will be of a size suitable for injection. In one embodiment, the size range for microparticles is from about one to about 50 microns in diameter.

As defined herein, a sustained release of a biologically active agent is a release of the biologically active agent (e.g., bromfenac) from a sustained release delivery system or composition. The release occurs over a period which is longer than that period during which a therapeutically significant amount of the biologically active agent would be available following direct administration of a solution of the biologically active agent. In one embodiment, a sustained release occurs over a period of greater than six to twelve hours such as about twenty-four hours or longer. A sustained release of biologically active agent can be a continuous or a discontinuous release, with relatively constant or varying rates of release. The continuity of release and level of release can be affected by the type of polymer composition used (e.g., monomer ratios, molecular weight, and varying combinations of polymers), agent loading, and/or selection of excipients to produce the desired effect.

As used herein the term "treating" or "treatment" refers to reducing, ameliorating reversing, alleviating, inhibiting the progress of, or preventing a disease or a medical condition of the eye itself or the tissue surrounding the eye or the symptoms associated therewith. The term also encompasses prophylaxis, therapy and cure. The subject receiving "treatment," or whom undergoes "treating" is any mammal in need of such treatment for (eye-related inflammation or inflammatory conditions), including primates, in such as humans, and other mammals such as equines, cattle, swine and sheep; and poultry and domesticated mammals and pets in general.

The term "therapeutically effective amount" as used herein means that the amount of a composition elicits a beneficial biological or medicinal response in a tissue, system, animal or human. For example, a therapeutically effective amount of a composition of the invention is a dose which leads to a clinically detectable improvement or treatment (as defined above) of the eye of a subject suffering from an inflammatory eye condition or disease.

As used herein, the term "about" refers to an approximation of a stated value within an acceptable range, e.g. +/−5% of the stated value.

It is an aspect of the present invention to provide novel ophthalmic compositions for treating inflammation and inflammatory conditions of the eye; such compositions include bromfenac and a flowable mucoadhesive polymer to increase the retention of bromfenac in the eye for a longer period of time.

It is a further aspect of the invention to provide a novel sustained release delivery system for bromfenac, which includes bromfenac and a flowable mucoadhesive polymer. It is an object of this invention to provide a novel sustained release delivery system for topical ophthalmic delivery of bromfenac.

A further aspect of this invention is to provide novel bromfenac compositions and sustained release ophthalmic delivery systems suitable for administration at intervals of once daily or less often, e.g., once per every two to three days.

Yet another aspect of this invention is to provide a method for convenient therapeutic treatment using a composition or a delivery system including bromfenac and a flowable mucoadhesive polymer, which has a prolonged release time for bromfenac while facilitating a high absorption and retention of bromfenac in the eye over the release-time period.

A still further aspect of this invention is to provide novel methods for treating, ameliorating or reducing inflammation or inflammatory conditions of the eye by providing a composition or a delivery system containing bromfenac and a flowable mucoadhesive polymer, which has a prolonged release time for bromfenac, while facilitating a high absorption and retention of bromfenac by the eye over the release time period.

According to one aspect of the present invention there is provided a method of treating inflammation or inflammatory conditions of the eye or an ocular disease, injury or disorder in a patient by administering a topical ophthalmic formulation described herein. Furthermore the method may include a dosing regime of once, to two times daily administration into said eye to treat the pain and/or inflammation associated with said ocular disease, injury or disorder. In one embodiment, the dosing is once a day bromfenac formulation.

A further aspect of the present invention is a therapeutic method wherein said ocular disease, injury or disorder is caused by surgery, physical damage to the eye, glaucoma, macular degeneration, or diabetic retinopathy. The formulation of bromfenac, in accordance with the compositions or methods of the invention, can be used to treat retina conditions (e.g., macular edema, macular degeneration, etc.) since topical application of the inventive compositions results in high concentrations of the drug, i.e., bromfenac, in the retina. A still further aspect of the present invention is to use the bromfenac formulations of the invention to treat ocular disease, injury or disorder wherein the ocular disease, injury or disorder is one caused by vascular leakage in the eye or by inflammation in the eye. Examples of conditions related to inflammation in the eye include, but are not limited to the following: surgical trauma; dry eye; allergic conjunctivitis; viral conjunctivitis; bacterial conjunctivitis; blepharitis; anterior uveitis; injury from a chemical; radiation or thermal burn; injury from penetration of a foreign body, pain in or around the eye, redness especially accompanied by pain in the eye; light sensitivity; seeing halos (colored circles or halos around lights); bulging (protrusion) of the eye; swelling of eye tissues; discharge, crusting or excessive tearing; eyelids stuck together, blood inside the front of the eye (on the colored part) or white of the eye); cataracts; pain and inflammation associated with wearing contact lenses; corneal-associated condition; conjunctival tumor excision; conjunctivitis known as Pink Eye; cornea edema after cataract surgery; corneal clouding; corneal transplantation; corneal ulcer; dry eye syndrome; dystrophies; condition associated with excimer laser phototherapeutic keratectomy; herpes simplex keratitis; keratoconus; pterygium; recurrent erosion syndrome; eye movement disorder; glaucoma; ocular oncology; oculoplastic condition resulted from cosmetic surgery, enucleation, eyelid and orbit injuries, ectropion, entropion, graves' disease, involuntary eyelid blinking; condition associated with refractive surgery; and retinal condition.

Retinal conditions include, but are not limited to, age related macular degeneration, AIDS-related ocular disease (e.g., CMV retinitis), birdshot retinochoroidopathy (BR), choroidal melanoma, coats disease, cotton wool spots, diabetic retinopathy, diabetic macular edema, cystoid macular edema, lattice degeneration, macular disease (e.g., macular degeneration, hereditary macular dystrophy, macular edema, macular hole, macular pucker, central serous chorioretinopathy), ocular histoplasmosis syndrome (OHS), posterior vitreous detachment, retinal detachment, retinal artery obstruction, retinal vein occlusion, retinoblastoma, retinopathy of prematurity (ROP), retinitis pigmentosa, retinoschisis (acquired and x-linked), stargardt's disease, toxoplasmosis (affecting retina) and uveitis.

Bromfenac is a non-steroidal anti-inflammatory agent which has the structural formula of

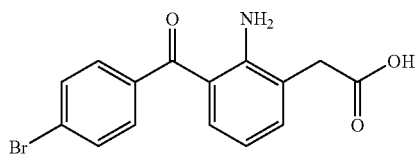

The above compound to be used in accordance with the invention may be in a salt form or a hydrated form or both. The salt forms include alkali metal salts such as sodium salt and potassium salt, alkaline earth metal salts such as calcium salt and magnesium salt, among others, and any salt may suitably be used, provided that it can attain the object of the invention. The hydrated forms include monohydrate, sesquihydrate (1.5 H$_2$O), dihydrate, pentahydrate and any other hydrate forms may suitably be used, provided that it can attain the object of the invention.

The present invention also provides kits including a composition having bromfenac and a flowable mucoadhesive polymer for application to the eye of a mammal. The kit further includes instructions for how use the composition, eye dropper and other useful paraphernalia for topical delivery to the eye.

In one embodiment, according to any of the above aspects of the invention, the composition of the invention has a pH of about 7.4 to about 8.5; in other embodiments the pH is about 8.3.

In one embodiment, according to any of the above aspects of the invention, the bromfenac content of the compositions of the invention is about 0.005% to about 0.5% by weight of the composition. In another embodiment, the bromfenac content of the compositions is about 0.01% to about 0.2% by weight of the composition. In another embodiment, the bromfenac content of the compositions is about 0.01% to about 0.09% by weight of the composition. In another embodiment, the bromfenac content of the compositions is about 0.045% to about 0.09% by weight of the composition In one embodiment, according to any of the above aspects of the invention, the viscosity of the compositions of the invention is in the range of about 1,000 to about 2,000 cps. In another embodiment, the viscosity of the composition of the invention is about 1,500 cps. When formulated as a topical ophthalmic delivery system, the viscosity of the composition of the invention is desirably in a range suitable for administration to the eye in drop form, such as a viscosity from about 1,000 to about 2,000 cps.

In one embodiment, according to any of the above aspects of the invention, the bromfenac is retained in or carried with the flowable mucoadhesive polymer. The flowable mucoadhesive polymer increases the retention of bromfenac in the eye for a longer period of time. In another embodiment, the entire bromfenac content of the composition of the invention is in aqueous solution.

In one embodiment, according to any of the above aspects of the invention, a percentage of bromfenac content of the compositions of the invention is in aqueous solution with the polymer while the remaining bromfenac remains in suspension with the polymer. In another embodiment, the bromfenac mixed with the polymer carrier can be in suspension to act as a reservoir established in suspension at the pH of the formulation. The amount established in suspension may vary depending on therapeutic needs, but it will be at least an amount sufficient to have a therapeutic effect on the eye upon delayed release from the suspension over a period of time. A sufficient amount of agent will also be present in solution to have an immediate therapeutic effect upon topical ophthalmic application. For example, about 80% to about 90% of the total bromfenac contained in the mixture will be in suspension, but this may vary depending on how much of the agent is desired for sustained delivery and the duration of delivery desired. The amount of bromfenac in suspension may, for instance, range from about 70% to about 99% or about 10% to about 99% by weight of the total amount of bromfenac contained in the mixture. The compositions will not, however, have 100% of bromfenac in suspension. Some amount will be in solution to provide the immediate therapeutic effect. In certain embodiments, the concentration of bromfenac and the pH of the composition is selected to ensure that a sufficient amount of bromfenac is in suspension to provide a therapeutic effect upon delayed deliver. In this way, the portion of the agent in solution is immediately available for therapeutic effect, while the portion in suspension serves as a reservoir and is released slowly over time.

In some embodiments, according to any of the above aspects of the invention, the flowable mucoadhesive polymer content of the composition of the invention is about 0.5% to about 1.5% by weight of the composition. In other embodiments, the flowable mucoadhesive polymer content of the composition of the invention is about 0.8% to about 1.0% by weight of the composition. In another embodiment, the flowable mucoadhesive polymers of the invention are crosslinked carboxy-vinyl polymers as carboxy-containing polymers. Suitable carboxy-containing polymers for use in the present invention and method for making them are described in U.S. Pat. No. 5,192,535 to Davis et al. which is hereby incorporated, in its entirety, by reference and relied upon. These polymer carriers include lightly crosslinked carboxy-containing polymers such as polycarbophil, or Carbopols®, dextran, cellulose derivatives, polyethylene glycol 400 and other polymeric demulcents such as polyvinylpyrolidone, polysaccaride gels and Gelrite®. In another embodiment, a carboxy-containing polymer system known by the tradename DuraSite® is used. DuraSite® is a lightly crosslinked polymer containing polycarbophil which is a sustained release topical ophthalmic delivery system that releases the drug at a controlled rate.

The lightly crosslinked polymers of acrylic acid or the like used in practicing this invention are, in general, well known in the art. In one embodiment such polymers are ones prepared from at least about 90% or from about 95% to about 99.9% by weight, based on the total weight of monomers present, of one or more carboxyl-containing monoethylenically unsaturated monomers. Acrylic acid is a carboxyl-containing monoethylenically unsaturated monomer, but other unsaturated, polymerizable carboxyl-containing monomers, such as methacrylic acid, ethacrylic acid, .beta.-methylacrylic acid (crotonic acid), cis-.alpha.-methylcrotonic acid (angelic acid), trans-.alpha.-methylcrotonic acid (tiglic acid), alpha.-butylcrotonic acid, .alpha.-phenylacrylic acid, .alpha.-benzylacrylic acid, alpha.-cyclohexylacrylic acid, .beta.-phenylacrylic acid (cinnamic acid), coumaric acid (o-hydroxycinnamic acid), umbellic acid (p-hydroxycoumaric acid), and the like can be used in addition to or instead of acrylic acid.

Such polymers are crosslinked by using a small percentage, i.e., less than about 5%, such as from about 0.5% or from about 0.1% to about 5%, or from about 0.2% to about 1%, based on the total weight of monomers present, of a polyfunctional crosslinking agent. Included among such crosslinking agents are non-polyalkenyl polyether difunctional crosslinking monomers such as divinyl glycol; 2,3-dihydroxyhexa-1,5-diene; 2,5-dimethyl-1,5-hexadiene; divinylbenzene; N,N-diallylacrylamide; N,N-diallylmethacrylamide and the like. Also included are polyalkenyl polyether crosslinking agents containing two or more alkenyl ether groupings per molecule, or alkenyl ether groupings containing terminal H$_2$ C=C< groups, prepared by etherifying a polyhydric alcohol containing at least four carbon atoms and at least three hydroxyl groups with an alkenyl halide such as allyl bromide or the like, e.g., polyallyl sucrose, polyallyl pentaerythritol, or the like; see, e.g., Brown U.S. Pat. No. 2,798,053, which incorporated herein by reference in its entirety. Diolefinic non-hydrophilic macromeric crosslinking agents having molecular weights of from about 400 to about 8,000, such as insoluble di- and polyacrylates and methacrylates of diols and polyols, diisocyanate-hydroxyalxyl acrylate or methacrylate reaction products, and reaction products of isocyanate terminated prepolymers derived from polyester diols, polyether diols or polysiloxane diols with hydroxyalkylmethacrylates, and the like, can also be used as the crosslinking agents; see, e.g., Mueller et al. U.S. Pat. Nos. 4,192,827 and 4,136,250, which incorporated herein by reference in its entirety.

The lightly crosslinked polymers can of course be made from a carboxyl-containing monomer or monomers as the sole monoethylenically unsaturated monomer present, together with a crosslinking agent or agents. They can also be polymers in which up to about 40%, or from about 0% to about 20% by weight, of the carboxyl-containing monoethylenically unsaturated monomer or monomers has been replaced by one or more non-carboxyl-containing monoethylenically unsaturated monomers containing only physiologically and ophthalmologically innocuous substituents, including acrylic and methacrylic acid esters such as methyl methacrylate, ethyl acrylate, butyl acrylate, 2-ethylhexylacrylate, octyl methacrylate, 2-hydroxyethyl-methacrylate, 3-hydroxypropylacrylate, and the like, vinyl acetate, N-vinylpyrrolidone, and the like; see Mueller et al. U.S. Pat. No. 4,548,990, which incorporated herein by reference in its entirety, for a more extensive listing of such additional monoethylenically unsaturated monomers. In one embodiment, polymers are lightly crosslinked acrylic acid polymers wherein the crosslinking monomer is 2,3-dihydroxyhexa-1,5-diene or 2,3-dimethylhexa-1,5-diene.

The lightly crosslinked polymers used in practicing this invention are prepared by suspension or emulsion polymerizing the monomers, using conventional free radical polymerization catalysts, to a dry particle size of not more than about 50 μm in equivalent spherical diameter; e.g., to provide dry polymer particles ranging in size from about 1 to about 30 μm, or from about 3 to about 20 μm, in equivalent spherical diameter. In general, such polymers will range in molecular weight estimated to be about 25,000 to about 4,000,000, or about 500,000 to about 2,000,000.

According to any of the above aspects of the invention, the composition of the invention is an aqueous mixture that can also contain amounts of suspended lightly crosslinked polymer particles ranging from about 0.5% to about 1.5% by weight, or from about 0.8% to about 1.0% by weight, based on the total weight of the aqueous mixture. The aqueous mixture can be an aqueous solution of bromfenac and a flowable mucoadhesive polymer or an aqueous suspension of bromfenac and a flowable mucoadhesive polymer. In certain embodiments, the composition of the invention is prepared using pure, sterile water, such as deionized or distilled, having no physiologically or ophthalmologically harmful constituents, and is adjusted to a pH of from about 7.4 to about 8.5, in some embodiments from about 8.2 to about 8.4, and in other embodiments to a pH of about 8.3 using any physiologically and ophthalmologically acceptable pH adjusting acid, base or buffer, e.g., acids such as acetic, boric, citric, lactic, phosphoric, hydrochloric, or the like, bases such as sodium hydroxide, sodium phosphate, sodium borate, sodium citrate, sodium acetate, sodium lactate, THAM (trishydroxymethylaminomethane), or the like and salts and buffers such as citrate/dextrose, sodium bicarbonate, ammonium chloride and mixtures of the aforementioned acids and bases. For example, bromfenac or its salt at may be dissolved and added by sterile filtration to a preparation containing sodium chloride, DuraSite® and surfactant. This mixture may then be adjusted to the appropriate pH by known techniques, for example by the addition of sodium hydroxide. Other methods will be apparent to one skilled in the art.

When formulating the composition of the invention as either an aqueous solution or an aqueous suspension, the osmolality can be adjusted to from about 10 mOsm/kg to about 400 mOsm/kg, using appropriate amounts of physiologically and ophthalmologically acceptable salts. Sodium chloride approximates physiologic fluid, and amounts of sodium chloride ranging from about 0.01% to about 1% by weight, or from about 0.05% to about 0.45% by weight, based on the total weight of the aqueous suspension, provide osmolalities within the above-stated ranges. Equivalent amounts of one or more salts made up of cations such as potassium, ammonium and the like and anions such as chloride, citrate, ascorbate, borate, phosphate, bicarbonate, sulfate, thiosulfate, bisulfate, sodium bisulfate, ammonium sulfate, and the like can also be used in addition to or instead of sodium chloride to achieve osmolalities within the above-stated ranges. Sugars like mannitol, dextrose, glucose or other polyols may be added to adjust the osmolality.

The amounts of flowable mucoadhesive polymer, the pH, and the osmotic pressure chosen from within the above-stated ranges are correlated with one another and with the degree of crosslinking of the polymer to give aqueous solutions or suspensions having viscosities ranging from about 1,000 to about 2,000 or 5,000 to about 20,000 cps respectively, as measured at room temperature (about 25° C.) using a Brookfield Digital LVT Viscometer equipped with a number 25 spindle and a 13R small sample adapter at 12 rpm. The compositions of the present invention have a viscosity that is suited for the selected route of administration. Alternatively, the viscosity can be 1000 to 3400 cps as measured with a Brookfield cone and plate viscosity DV-II+ with the spindle No. CP-52 at 6 rpm.

In one embodiment, according to any of the above aspects of the invention, the compositions of the present invention ordinarily contain one or more surfactants and, if desired, one or more adjuvants, including additional medicaments, buffers, antioxidants, tonicity adjusters, preservatives, thickeners or viscosity modifiers, and the like. Additives in the formulation may desirably include sodium chloride, EDTA (disodium edetate), and BAC (benzalkonium chloride) or sorbic acid, or both.

Compositions delivered by means of the sustained release medicament delivery system of this invention typically have residence times in the eye ranging from about 8 to about 24 hours. The bromfenac contained in these compositions is released from the composition at rates that depend on such factors as bromfenac itself and its physical form, the extent of drug loading and the pH of the system, as well as on any drug delivery adjuvants, such as ion exchange resins compatible with the ocular surface, which may also be present in the composition. In one embodiment, according to any of the aspects of the present invention, the composition of the invention provides a sustained concentration of bromfenac of between $10^{-8}$ and $10^{-4}$ M, in another embodiment between $10^{-7}$ and $10^{-5}$ M, in the aqueous or treated tissue of the eye for at least two hours, and in certain embodiments, at least three hours. In another embodiment, the composition of the invention provides sustained concentration of bromfenac of between $10^{-8}$ and $10^{-4}$ M, or between $10^{-7}$ and $10^{-5}$ M, in the aqueous or treated tissue of the eye for at least two hours, or at least three hours.

Ophthalmic compositions of the present invention may be formulated so that they retain the same or substantially the same viscosity in the eye that they had prior to administration to the eye. Alternatively, ophthalmic suspensions of the present invention may be formulated so that there is increased gelation upon contact with tear fluid. For instance, when a formulation containing DuraSite® is administered to the eye, the DuraSite® system swells upon contact with tears. This gelation or increase in gelation leads to a slower release rate of bromfenac, thereby extending the residence time of the composition in the eye. These events eventually leads to increased patient comfort, increase in the time bromfenac is in contact with the eye tissues, thereby increasing the extent of drug absorption and duration of action of the formulation in the eye.

In an embodiment, according to any of the above aspects of the invention, the invention relates to a composition or method for combination therapy of the eye of a mammal including: an ophthalmic composition having a therapeutically effective amount of bromfenac, a therapeutically effective amount of ketorolac and a flowable mucoadhesive polymer such as DuraSite®, wherein the composition has a viscosity formulated for administration to the eye of a mammal in drop form. In an embodiment, ketorolac is included in the composition of the invention in an amount of about 0.01% to about 1% by weight of the composition. In another embodiment, ketorolac is included in the composition of the invention in an amount of about 0.4% to about 0.5% by weight of the composition. In another embodiment, the invention relates to a composition or method for combination therapy of the eye of a mammal including: an ophthalmic composition having a therapeutically effective amount of bromfenac, a flowable mucoadhesive polymer such as DuraSite® and one or more additional non-steroidal anti-inflammatory agent such as, for example, ketorolac. In another embodiment, the invention relates to a composition or method for combination therapy of the eye of a mammal including: an ophthalmic composition having a therapeutically effective amount of bromfenac, a flowable mucoadhesive polymer such as DuraSite® and one or more steroidal anti-inflammatory agent. In another embodiment, the invention relates to a composition or method for combination therapy of the eye of a mammal including: an ophthalmic composition having a therapeutically effective amount of bromfenac, a flowable mucoadhesive polymer such as DuraSite® and one or more antibacterial agent. In another embodiment, relating to any of the above aspects, the invention relates to a composition or method for combination therapy of the eye of a mammal including: an ophthalmic composition having a therapeutically effective amount of bromfenac, a flowable mucoadhesive polymer such as DuraSite® and an additional therapeutically active agent selected from the group consisting of antibacterial antibiotic agent, synthetic antibacterial agent, antifungal antibiotic agent, synthetic antifungal agent, antineoplastic agent, steroidal anti-inflammatory agent, non-steroidal anti-inflammatory agent, anti-allergic agent, glaucoma-treating agent, antiviral agent and anti-mycotic agent.

In one embodiment, according to any of the above aspects of the invention, the compositions of the invention can include, in addition to bromfenac, one or more other active ingredients such as other NSAIDs. Suitable NSAIDs for combination therapy are, for example, aspirin, benoxaprofen, benzofenac, bucloxic acid, butibufen, carprofen, cicloprofen, cinmetacin, clidanac, clopirac, diclofenac, diflupredinate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketoprofen, lactorolac, lonazolac, metiazinic, miroprofen, nepafenac, naproxen, norketotifen, oxaprozin, oxepinac, phenacetin, pirprofen, pirazolac, protizinic acid, sulindac, suprofen, tiaprofenic acid, tolmetin, and zomepirac.

Unless the intended purpose of use is affected adversely, the ophthalmic formulation of the present invention can further comprise one or more additional therapeutically-active agents. Specific therapeutically-active agents include, but are not limited to: antibacterial antibiotics, synthetic antibacterials, antifungal antibiotics, synthetic antifungals, antineoplastic agents, steroidal anti-inflammatory agents, non-steroidal anti-inflammatory agents, anti-allergic agents, glaucoma-treating agents, antiviral agents, and anti-mycotic agents. Further contemplated are any derivatives of the therapeutically-active agents which may include, but not be limited to: analogs, salts, esters, amines, amides, alcohols and acids derived from an agent of the invention and may be used in place of an agent itself.

Examples of the antibacterial antibiotics include, but are not limited to: aminoglycosides (e.g., amikacin, apramycin, arbekacin, bambermycins, butirosin, dibekacin, dihydrostreptomycin, fortimicin(s), gentamicin, isepamicin, kanamycin, micronomicin, neomycin, neomycin undecylenate, netilmicin, paromomycin, ribostamycin, sisomicin, spectinomycin, streptomycin, tobramycin, trospectomycin), amphenicois (e.g., azidamfenicol, chloramphenicol, florfenicol, thiamphenicol), ansamycins (e.g., rifamide, rifampin, rifamycin sv, rifapentine, rifaximin), .beta.-lactams (e.g., carbacephems (e.g., loracarbef), carbapenems (e.g., biapenem, imipenem, meropenem, panipenem), cephalosporins (e.g., cefaclor, cefadroxil, cefamandole, cefatrizine, cefazedone, cefazolin, cefcapene pivoxil, cefclidin, cefdinir, cefditoren, cefepime, cefetamet, cefixime, cefmenoxime, cefodizime, cefonicid, cefoperazone, ceforanide, cefotaxime, cefotiam, cefozopran, cefpimizole, cefpiramide, cefpirome, cefpodoxime proxetil, cefprozil, cefroxadine, cefsulodin, ceftazidime, cefteram, ceftezole, ceftibuten, ceftizoxime, ceftriaxone, cefuroxime, ceifuzonam, cephacetrile sodium, cephalexin, cephaloglycin, cephaloridine, cephalosporin, cephalothin, cephapirin sodium, cephradine, pivcefalexin), cephamycins (e.g., cefbuperazone, cefmetazole, cefininox, cefotetan, cefoxitin), monobactams (e.g., aztreonam, carumonam, tigemonam), oxacephems, flomoxef, moxalactam), penicillins (e.g., amdinocillin, amdinocillin pivoxil, amoxicillin, ampicillin, apalcillin, aspoxicillin, azidocillin, azlocillin, bacampicillin, benzylpenicillinic acid, benzylpenicillin sodium, carbenicillin, carindacillin, clometocillin, cloxacillin, cyclacillin, dicloxacillin, epicillin, fenbenicillin, floxacillin, hetacillin, lenampicillin, metampicillin, methicillin sodium, mezlocillin, nafcillin sodium, oxacillin, penamecillin, penethamate hydriodide, penicillin g benethamine, penicillin g benzathine, penicillin g benzhydrylamine, penicillin g calcium, penicillin g hydrabamine, penicillin g potassium, penicillin g procaine, penicillin n, penicillin o, penicillin v, penicillin v benzathine, penicillin v hydrabamine, penimepicycline, phenethicillin potassium, piperacillin, pivampicillin, propicillin, quinacillin, sulbenicillin, sultamicillin, talampicillin, temocillin, ticarcillin), other (e.g., ritipenem), lincosamides (e.g., clindamycin, lincomycin), macrolides (e.g., azithromycin, carbomycin, clarithromycin, dirithromycin, erythromycin, erythromycin acistrate, erythromycin estolate, erythromycin glucoheptonate, erythromycin lactobionate, erythromycin propionate, erythromycin stearate, josamycin, leucomycins, midecamycins, miokamycin, oleandomycin, primycin, rokitamycin, rosaramicin, roxithromycin, spiramycin, troleandomycin), polypeptides (e.g., amphomycin, bacitracin, capreomycin, colistin, enduracidin, enviomycin, fusafungine, gramicidin s, gramicidin(s), mikamycin, polymyxin, pristinamycin, ristocetin, teicoplanin, thiostrepton, tuberactinomycin, tyrocidine, tyrothricin, vancomycin, viomycin, virginiamycin, zinc bacitracin), tetracyclines (e.g., apicycline, chlortetracycline, clomocycline, demeclocycline, doxycycline, guamecycline, lymecycline, meclocycline, methacycline, minocycline, oxytetracycline, penimepicycline, pipacycline, rolitetracycline, sancycline, tetracycline), and others (e.g., cycloserine, mupirocin, tuberin).

Examples of the synthetic antibacterials include, but are not limited to: 2,4-diaminopyrimidines (e.g., brodimoprim, tetroxoprim, trimethoprim), nitrofurans (e.g., furaltadone, furazolium chloride, nifuradene, nifuratel, nifurfoline, nifurpirinol, nifurprazine, nifurtoinol, nitrofurantoin), quinolones and analogs (e.g., cinoxacin, ciprofloxacin, clinafloxacin, difloxacin, enoxacin, fleroxacin, flumequine, grepafloxacin, lomefloxacin, miloxacin, nadifloxacin, nalidixic acid, norfloxacin, ofloxacin, oxolinic acid, pazufloxacin, pefloxacin, pipemidic acid, piromidic acid, rosoxacin, rufloxacin, sparfloxacin, temafloxacin, tosufloxacin, trovafloxacin), sulfonamides (e.g., acetyl sulfamethoxypyrazine, benzylsulfamide, chloramine-b, chloramine-t, dichloramine-t, n.sup.2-formylsulfisomidine, n.sup.4-.beta.-d-glucosylsulfanilamide, mafenide, 4'-(methylsulfamoyl) sulfanilanilide, noprylsulfamide, phthalylsulfacetamide, phthalylsulfathiazole, salazosulfadimidine, succinylsulfathiazole, sulfabenzamide, sulfacetamide, sulfachlorpyridazine, sulfachrysoidine, sulfacytine, sulfadiazine, sulfadicramide, sulfadimethoxine, sulfadoxine, sulfaethidole, sulfaguanidine, sulfaguanol, sulfalene, sulfaloxic acid, sulfarnerazine, sulfameter, sulfamethazine, sulfamethizole, sulfamethomidine, sulfamethoxazole, sulfamethoxypyridazine, sulfametrole, sulfamidocchrysoidine, sulfamoxole, sulfanilamide, 4-sulfanilamidosalicylic acid, n.sup.4-sulfanilylsulfanilamide, sulfanilylurea, n-sulfanilyl-3,4-xylamide, sulfanitran, sulfaperine, sulfaphenazole, sulfaproxyline, sulfapyrazine, sulfapyridine, sulfasomizole, sulfasymazine, sulfathiazole, sulfathiourea, sulfatolamide, sulfisomidine, sulfisoxazole) sulfones (e.g., acedapsone, acediasulfone, acetosulfone sodium, dapsone, diathymosulfone, glucosulfone sodium, solasulfone, succisulfone, sulfanilic acid, p-sulfanilylbenzylamine, sulfoxone sodium, thiazolsulfone), and others (e.g., clofoctol, hexedine, methenamine, methenamine anhydromethylene-citrate, methenamine hippurate, methenamine mandelate, methenamine sulfosalicylate, nitroxoline, taurolidine, xibornol).

Examples of the steroidal anti-inflammatory agents include, but are not limited to: 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, and triamcinolone hexacetonide.

Examples of the antifungal antibiotics include, but are not limited to: polyenes (e.g., amphotericin b, candicidin, dennostatin, filipin, fungichromin, hachimycin, hamycin, lucensomycin, mepartricin, natamycin, nystatin, pecilocin, perimycin), others (e.g., azaserine, griseofulvin, oligomycins, neomycin undecylenate, pyrrolnitrin, siccanin, tubercidin, viridin). Examples of the synthetic antifungals include, but are not limited to: allylamines (e.g., butenafine, naftifine, terbinafine), imidazoles (e.g., bifonazole, butoconazole, chlordantoin, chlormiidazole, clotrimazole, econazole, enilconazole, fenticonazole, flutrimazole, isoconazole, ketoconazole, lanoconazole, miconazole, omoconazole, oxiconazole nitrate, sertaconazole, sulconazole, tioconazole), thiocarbamates (e.g., tolciclate, tolindate, tolnaftate), triazoles (e.g., fluconazole, itraconazole, saperconazole, terconazole) others (e.g., acrisorcin, amorolfine, biphenamine, bromosalicylchloranilide, buclosamide, calcium propionate, chlorphenesin, ciclopirox, cloxyquin, coparaffinate, diamthazole dihydrochloride, exalamide, flucytosine, halethazole, hexetidine, loflucarban, nifuratel, potassium iodide, propionic acid, pyrithione, salicylanilide, sodium propionate, sulbentine, tenonitrozole, triacetin, ujothion, undecylenic acid, zinc propionate).

In general, ophthalmic formulations suitable for topical ophthalmic administration can be formulated and administered in accordance with techniques familiar to persons skilled in the art. The finished formulations are stored in opaque or brown containers to protect them from light exposure, and under an inert atmosphere. These compositions can be packaged in preservative-free, single-dose non-reclosable/reclosable containers or kits. This permits a single dose of the medicament to be delivered to the eye as a drop, with the container then being discarded after use. Such containers eliminate the potential for preservative-related irritation and sensitization of the corneal epithelium, as has been observed to occur particularly from ophthalmic medicaments containing mercurial preservatives. Multiple dose containers can also be used, if desired, particularly since the relatively low viscosities of the compositions of this invention permit constant, accurate dosages to be administered dropwise to the eye as many times each day as necessary. In those suspensions where preservatives are to be included, suitable preservatives are chlorobutanol, polyquat, benzalkonium chloride, cetyl bromide, sorbic acid and the like.

Another embodiment of the present invention includes the method of treating ocular inflammation and/or pain in a patient in need with one of the ophthalmic formulations described above, wherein said inflammation and/or pain is caused by surgical trauma, and wherein said treatment comprises treating the patient once, or twice a day. An additional embodiment of the present invention includes the method of treating ocular pain and/or inflammation in a patient in need thereof, wherein said inflammation and accompanying pain is the result of cataract surgery or one of many refractive eye surgical techniques, and wherein said treatment comprises treating the patient once or twice daily with a formulation herein.

An additional embodiment of the present invention includes the method of treating ocular pain and/or inflammation in a patient in need thereof, wherein said inflammation and accompanying pain is the result of allergic, viral or bacterial conjunctivitis, and wherein said treatment comprises treating the patient with any of the disclosed formulations.

An additional embodiment of the present invention includes a method treating ocular pain and/or inflammation associated with allergic, viral or bacterial conjunctivitis with one of the topical ophthalmic formulations of the invention. An additional embodiment may include one or more additional active ingredients as part of the formulation, such additional actives may include, but are not limited to, antihistamines and/or antibacterials and/or antimicrobial compounds, to further assist with the treatment of the conjunctivitis condition.

An additional embodiment of the present invention includes a method for treating an eye wherein its normal condition has been disrupted or changed comprising administering to said eye one to six times daily the formulation or composition of the invention. An additional embodiment of the present invention includes a method for treating postoperative inflammation and/or pain in patients who have undergone cataract extraction comprising the once, twice or up to six times daily administration of a selected formulation into the effected eye.

For example, in one embodiment, the methods of the invention encompass a process for therapeutic treatment of an inflammatory condition of the eye in a mammal including: (a) providing an ophthalmic composition comprising bromfenac in an amount of about 0.005% to about 0.5% by weight of the composition and a flowable mucoadhesive polymer in an amount of about 0.5% to about 1.5% by weight of the composition; (b) administering said composition to the eye of a mammal in need thereof to treat inflammation or inflammatory conditions of the eye. In a related embodiment, the ophthalmic composition further includes a therapeutically active agent selected from the group consisting of antibacterial antibiotic agent, synthetic antibacterial agent, antifungal antibiotic, synthetic antifungal agent, antineoplastic agent, steroidal anti-inflammatory agent, non-steroidal anti-infaimatory agent, anti-allergic agent, glaucoma-treating agent, antiviral agent and anti-mycotic agent. In another related embodiment, wherein the non-steroidal anti-inflammatory agent is ketorolac. In an embodiment, ketorolac is included in the composition of the invention in an amount of about 0.01% to about 1% by weight of the composition. In another embodiment, ketorolac is included in the composition of the invention in an amount of about 0.4% to about 0.5% by weight of the composition.

The inflammatory conditions for which the compositions and methods of the invention can be use are, but not limited to, surgical trauma; dry eye; allergic conjunctivitis; viral conjunctivitis; bacterial conjunctivitis; blepharitis; anterior uveitis; injury from a chemical; radiation or thermal burn; injury from penetration of a foreign body, pain in or around the eye, redness especially accompanied by pain in the eye; light sensitivity; seeing halos (colored circles or halos around lights); bulging (protrusion) of the eye; swelling of eye tissues; discharge, crusting or excessive tearing; eyelids stuck together, blood inside the front of the eye (on the colored part) or white of the eye; cataracts; pain and inflammation associated with wearing contact lenses; corneal-associated condition; conjunctival tumor excision; conjunctivitis known as Pink Eye; cornea edema after cataract surgery; corneal clouding; corneal transplantation; corneal ulcer; dry eye syndrome; dystrophies; condition associated with excimer laser phototherapeutic keratectomy; herpes simplex keratitis; keratoconus; pterygium; recurrent erosion syndrome; eye movement disorder; glaucoma; ocular oncology; oculoplastic condition resulted from cosmetic surgery, enucleation, eyelid and orbit injuries, ectropion, entropion, graves' disease, involuntary eyelid blinking; condition associated with refractive surgery; and retinal condition.

The retinal condition for which the compositions and methods of the invention can be used are, but not limited to, macular degeneration, AIDS-related ocular disease, CMV retinitis, birdshot retinochoroidopathy (BR), choroidal melanoma, coats disease, cotton wool spots, diabetic retinopathy diabetic macular edema, cystoid macular edema, lattice degeneration, macular disease, macular degeneration, hereditary macular dystrophy, macular edema, macular hole, macular pucker, central serous chorioretinopathy, ocular histoplasmosis syndrome (OHS), posterior vitreous detachment, retinal detachment, retinal artery obstruction, retinal vein occlusion, retinoblastoma, retinopathy of prematurity (ROP), retinitis pigmentosa, retinoschisis (acquired and x-linked), stargardt's disease, toxoplasmosis of retina or uveitis.

In order that those skilled in the art can more fully appreciate aspects of this invention, the following Tables and examples are set forth. These examples are given solely for purposes of illustration and should not be considered as expressing limitations.

EXAMPLE 1

Polycarbophil (Noveon® AA-1) was slowly dispersed into a citrate buffer solution containing dissolved EDTA and sodium chloride at approximately 50% of the final batch size. The resulting dispersion, which had a pH of a bout 3.0 to 3.5, was stirred with an overhead stirrer until visibly well hydrated. The mixture was sterilized by autoclaving at 121° C. for 20 minutes. The pH was then brought up to approximately 4.0 to 4.4 with 2N sodium hydroxide. Bromfenac sodium was dissolved in a mannitol solution containing dissolved benzalkonium chloride and Poloxamer 407 at approximately 20% of the final batch size. The resulting solution was then sterile filtered (0.22 μm filter) in to the polymer dispersion and stirred for 10 minutes. The pH of the bromfenac-polymer dispersion was brought to 8.3 with 2N sodium hydroxide. Sterile make up water was added to the formulation to final weight and mixed for at least 5 minutes. The formulation was aseptically filled into 5 ml bottles. See Table 1 for formulation composition.

TABLE 1

Composition of Bromfenac Formulations

| Excipient | Concentration (% w/w) | | |
| --- | --- | --- | --- |
| | Low Strength | Mid Strength | High Strength |
| Bromfenac | 0.045 | 0.09 | 0.36 |
| Polycarbophil | 0.9 | 0.9 | 0.9 |
| Citric acid | 0.2 | 0.2 | 0.2 |
| Citric acid | 0.2 | 0.2 | 0.2 |
| Sodium chloride | 0.14 | 0.14 | 0.14 |
| Sodium chloride | 0.1 | 0.1 | 0.1 |
| Poloxamer 407 | 0.1 | 0.1 | 0.1 |
| Manitol | 1.0 | 1.0 | 1.0 |
| Sodium hydroxide, 2N | q.s. to pH 8.3 | q.s. to pH 8.3 | q.s. to pH 8.3 |
| Water | q.s. to 100% | q.s. to 100% | q.s. to 100% |

EXAMPLE 2

In this example, the formulations of 0.09% and 0.045% bromfenac in DuraSite®, prepared according to Example 1, were compared with Xibrom® and Radio-Xibrom® in providing bromfenac to the aqueous humor of the eye in pigmented rabbits (n=6). In a first experiment, separately, the formulation of 0.09% bromfenac in DuraSite®, Xibrom® and Radio-Xibrom® (C carbon 14 labeled bromfenac in Xibrom from literature reference JOURNAL OF OCULAR PHARMACOLOGY AND THERAPEUTICS, 24(2), 2008, 392-398) were topically administered to pigmented rabbits in the amount of 1 drop per eye (approximately equal to about 25 microliters per eye). Xibrom was administered to one eye and the bromfenac DuraSite solution to the other. The concentrations of bromfenac in the aqueous humor of the eye were determined by removing the aqueous humor and measuring concentrations by LCMS (see FIG. 1A). In a second experiment, the bromfenac concentrations provided by 1 drop per eye of the formulation of 0.045% bromfenac in DuraSite®, Xibrom® and Radio-Xibrom® were separately monitored for 24 hours (see FIG. 1B). The results indicated that the exemplary formulations of the invention unexpectedly facilitated a high absorption and retention of bromfenac by the aqueous humor of the eye as compared with other Xibrom® and Radio-Xibrom®.

EXAMPLE 3

The formulation of 0.09% bromfenac in DuraSite®, prepared according to Example 1, was ophthalmically administered to pigmented rabbits in the same manner as Example 2, TID for a period of 14 days. At the end of the 14-day period, rabbits were sacrificed in accordance with the related regulatory and NIH guidelines for animal studies, and the concentration of bromfenac was measured using LCMS. In this experiment, the retina was separated from the choroid and tissue concentrations of bromfenac were measured. The concentration of bromfenac in the retina tissue from this 0.09% bromfenrac formulation on average, was found to be 34±10.4 ng per gram of tissue.

EXAMPLE 4

Polycarbophil (Noveon® AA-1) was slowly dispersed into a citrate buffer solution containing dissolved EDTA and sodium chloride at approximately 50% of the final batch size. The resulting dispersion, which had a pH of a bout 3.0 to 3.5, was stirred with an overhead stirrer until visibly well hydrated. The mixture was sterilized by autoclaving at 121° C. for 20 minutes. The pH was then brought up to approximately 4.0 to 4.4 with 2N sodium hydroxide. Bromfenac sodium (BF) and ketrolac tromethamine (KT) were dissolved in a mannitol solution containing dissolved benzalkonium chloride and Poloxamer 407 at approximately 20% of the final batch size. The resulting solution was then sterile filtered (0.22 μm filter) in to the polymer dispersion and stirred for 10 minutes. The pH of the bromfenac-ketorolac tromethamine-polymer dispersion was brought to 8.3 with 2N sodium hydroxide. Sterile make up water was added to the formulation to final weight and mixed for at least 5 minutes. The formulation was aseptically filled into 5 ml bottles containers. See Table 2 for composition and target attributes of the formulations.

TABLE 2

Compositions and Target Attributes of NSAID Formulations

| Excipient | 0.09% BF - DuraSite | 0.4% KT - DuraSite | 0.09% BF/0.4% KT - DuraSite |
|---|---|---|---|
| | Concentration (% w/w) | | |
| Bromfenac | 0.09 | N/A | 0.09 |
| Ketorolac Tromethamine | N/A | 0.4 | 0.4 |
| Polycarbophil | 0.9 | 0.9 | 0.9 |
| Benzalkonium chloride | 0.005 | 0.006 | 0.006 |
| Citric acid | 0.2 | 0.2 | 0.2 |
| Sodium citrate dihydrate | 0.14 | 0.14 | 0.14 |
| Mannitol | 1.0 | 1.0 | 1.0 |
| Edetate disodium dihydrate | 0.1 | 0.1 | 0.1 |
| Sodium chloride | 0.45 | 0.45 | 0.45 |
| Poloxamer 407 | 0.2 | N/A | N/A |
| Octoxynol 40 | N/A | 0.4 | 0.4 |
| 2N sodium hydroxide | q.s. to pH 8.3 | q.s. to pH 7.4 | q.s. to pH 8.3 |
| Water | q.s. to 100% | q.s. to 100% | q.s. to 100% |
| Attribute | | Target Value | |
| Bromfenac Assay | 0.09% | N/A | 0.09% |
| Ketorolac Tromethamine Assay | N/A | 0.4% | 0.4% |
| pH | 8.3 | 7.4 | 8.3 |
| Viscosity | 1500 cps | 1500 cps | 1500 cps |
| Osmolality | 290 mOsm/kg | 290 mOsm/kg | 290 mOsm/kg |

EXAMPLE 5

Polycarbophil (Noveon® AA-1) was slowly dispersed into a citrate buffer solution containing dissolved EDTA and sodium chloride at approximately 50% of the final batch size. The resulting dispersion, which had a pH of a bout 3.0 to 3.5, was stirred with an overhead stirrer until visibly well hydrated. The mixture was sterilized by autoclaving at 121° C. for 20 minutes. The pH was then brought up to approximately 4.0 to 4.4 with 2N sodium hydroxide. Bromfenac sodium and additional medicament was dissolved in a mannitol solution containing dissolved benzalkonium chloride and Poloxamer 407 at approximately 20% of the final batch size. The resulting solution was then sterile filtered (0.22 μm filter) in to the polymer dispersion and stirred for 10 minutes. The pH of the bromfenac drug-polymer dispersion was brought up to 8.0 with 2N sodium hydroxide. Sterile make up water was added to the formulation to final weight and mix for at least 5 minutes. The formulation was aseptically filled into 5 ml bottles containers. See Table 3 for formulation composition.

TABLE 3

Compositions of Bromfenac with Additional Medicaments

| Excipient | Concentration (%) | | |
|---|---|---|---|
| Bromfenac | 0.09 | 0.09 | 0.09 |
| Tobramycin | 0.3 | — | — |
| Dexamethasone phosphate | — | 0.125 | — |
| Doxycycline HCL | — | — | 0.3 |
| Polycarbophil | 0.9 | 0.9 | 0.9 |
| Benzalkonium chloride | 0.005 | 0.006 | 0.006 |
| Citric acid | 0.2 | 0.2 | 0.2 |
| Sodium citrate dihydrate | 0.14 | 0.14 | 0.14 |
| Mannitol | 1.0 | 1.0 | 1.0 |
| Edetate disodium dihydrate | 0.1 | 0.1 | 0.1 |
| Sodium chloride | 0.45 | 0.45 | 0.45 |
| Poloxamer 407 | 0.2 | 0.2 | 0.2 |
| 2N sodium hydroxide | q.s. to pH 8.0 | q.s. to pH 8.0 | q.s. to pH 8.0 |
| Water | q.s. to 100% | q.s. to 100% | q.s. to 100% |

The embodiments within the specification provide an illustration of embodiments of the invention and should not be construed to limit the scope of the invention. The skilled artisan readily recognizes that many other embodiments are encompassed by the invention.

We claim:

1. A topical ophthalmic composition formulated for application to the eye, said composition comprising a therapeutically effective amount of bromfenac and a flowable crosslinked carboxy-containing polycarbophil mucoadhesive polymer, wherein the composition has a viscosity in the range of about 1,000 to about 3,400 cps and a pH of about 7.4 to about 8.5.

2. The ophthalmic composition according to claim 1, wherein the composition further comprises a therapeutically effective amount of ketorolac.

3. The ophthalmic composition according to claim 1, wherein the flowable mucoadhesive polymer is in an amount of about 0.5% to about 1.5% by weight of the composition.

4. The ophthalmic composition according to claim 1, wherein bromfenac is in an amount of about 0.005% to about 0.5% by weight of the composition.

5. The ophthalmic composition according to claim 1, wherein the composition further comprises an additional therapeutically active agent selected from the group consisting of antibacterial antibiotic agent, synthetic antibacterial agent, antifungal antibiotic agent, synthetic antifungal agent, antineoplastic agent, steroidal anti-inflammatory agent, non-steroidal anti-inflammatory agent, anti-allergic agent, glaucoma-treating agent, antiviral agent and anti-mycotic agent.

6. The ophthalmic composition according to claim 5, wherein the additional therapeutic active agent is a non-steroidal anti-inflammatory agent selected from the group consisting of aspirin, benoxaprofen, benzofenac, bucloxic acid, butibufen, carprofen, cicloprofen, cinmetacin, clidanac, clopirac, diclofenac, difluprednate, etodolac, fenbufen, fenclofenac, fenclorac, fenoprofen, fentiazac, flunoxaprofen, furaprofen, flurbiprofen, furobufen, furofenac, ibuprofen, ibufenac, indomethacin, indoprofen, isoxepac, ketorolac, ketoprofen, lactorolac, lonazolac, metiazinic, miroprofen, naproxen, oxaprozin, oxepinac, phenacetin, pirprofen, pirazolac, protizinic acid, sulindac, suprofen, tiaprofenic acid, tolmetin, and zomepirac.

7. The ophthalmic composition according to claim 6, wherein the additional non-steroidal anti-inflammatory agent is ketorolac.

8. The ophthalmic composition according to claim 5, wherein the additional therapeutic active agent is a steroidal anti-inflammatory agent selected from the group consisting of 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamine-acetate, prednisolone sodium phosphate, prednisone, prednival, prednylidene, rimexolone, tixocortol, triamcinolone, triamcinolone acetonide, triamcinolone benetonide, and triamcinolone hexacetonide.

9. The topical ophthalmic composition of claim 1, wherein the viscosity of the composition is in the range of about 1,000 to about 2,000 cps.

10. The ophthalmic composition of claim 1, wherein the composition comprises from about 0.01 to 0.09 bromfenac by weight of the composition.

11. The ophthalmic composition of claim 10 wherein the composition has a pH of about 8.3.

12. An ophthalmic composition comprising a therapeutically effective amount of bromfenac, a therapeutically effective amount of ketorolac and a flowable crosslinked carboxy-containing polycarbophil mucoadhesive polymer, wherein
the composition has a viscosity in the range of about 1,000 to about 3,400 cps and is formulated for administration to the eye of a mammal in drop form, and
the composition has a pH of about 7.4 to about 8.5.

13. An ophthalmic composition comprising a therapeutically effective amount of bromfenac and a flowable mucoadhesive polymer, wherein:
the composition has a viscosity in the range of about 1,000 to about 3,400 cps and is formulated for administration to the eye of a mammal in drop form,
the composition further comprises at least one additional non-steroidal anti-inflammatory agent,
the flowable mucoadhesive polymer is a crosslinked carboxy-containing polycarbophil, and
the composition has a pH of about 7.4 to about 8.5.

14. An ophthalmic composition comprising a therapeutically effective amount of bromfenac and a flowable mucoadhesive polymer, wherein:
the composition has a viscosity in the range of about 1,000 to about 3,400 cps and is formulated for administration to the eye of a mammal in drop form,
the composition further comprises at least one steroidal anti-inflammatory agent,
the flowable mucoadhesive polymer is a crosslinked carboxy-containing polycarbophil, and
the composition has a pH of about 7.4 to about 8.5.

15. An ophthalmic composition comprising a therapeutically effective amount of bromfenac and a flowable mucoadhesive polymer, wherein:
the composition has a viscosity in the range of about 1,000 to about 3,400 cps and is formulated for administration to the eye of a mammal in drop form,
the composition further comprises at least one antibacterial agent,
the flowable mucoadhesive polymer is a crosslinked carboxy-containing polycarbophil, and
the composition has a pH of about 7.4 to about 8.5.

16. A method for therapeutic treatment of an inflammatory condition of the eye in a mammal comprising
administering the composition of claim 1 to the eye of a mammal in need thereof to treat inflammation or inflammatory conditions of the eye.

17. The method for therapeutic treatment of an inflammatory condition of the eye in a mammal according to claim 16, wherein the ophthalmic composition further comprises a therapeutically active agent selected from the group consisting of antibacterial antibiotic agent, synthetic antibacterial agent, antifungal antibiotic, synthetic antifungal agent, antineoplastic agent, steroidal anti-inflammatory agent, non-steroidal anti-inflammatory agent, anti-allergic agent, glaucoma-treating agent, antiviral agent and anti-mycotic agent.

18. The method for therapeutic treatment of an inflammatory condition of the eye in a mammal according to claim 17, wherein the therapeutically active agent is ketorolac.

19. The method for therapeutic treatment of an inflammatory condition of the eye in a mammal according to claim 16, wherein the inflammatory condition is selected from the group consisting of inflammatory conditions associated with surgical trauma; dry eye; allergic conjunctivitis; viral conjunctivitis; bacterial conjunctivitis; blepharitis; anterior uveitis; injury from a chemical; radiation or thermal burn; injury from penetration of a foreign body; pain in or around the eye; redness and pain in the eye; light sensitivity; seeing colored circles or halos around lights; protrusion of the eye; swelling of eye tissues; discharge, crusting or excessive tearing; eyelids stuck together; blood on the colored part or white of the eye; cataracts; wearing contact lenses; corneal-associated condition; conjunctival tumor excision; conjunctivitis; corneal edema associated with cataract surgery; corneal clouding; corneal transplantation; corneal ulcer; dry eye syndrome; dystrophies; excimer laser phototherapeutic keratectomy; herpes simplex keratitis; keratoconus; pterygium; recurrent erosion syndrome; eye movement disorder; glaucoma; ocular tumor; ocuplastic surgery; enucleation; eyelid or orbit injuries; ectropion; entropion; graves' disease; involuntary eyelid blinking; refractive surgery; and retinal condition.

20. The method for therapeutic treatment of an inflammatory condition of the eye in a mammal according to claim 16, wherein the inflammatory condition is associated with a retinal condition.

21. The method for therapeutic treatment of an inflammatory condition of the eye in a mammal according to claim 20, wherein the retinal condition is selected from the group consisting of age related macular degeneration, AIDS-related ocular disease, CMV retinitis, birdshot retinochoroidopathy (BR), choroidal melanoma, coats disease, cotton wool spots, diabetic retinopathy diabetic macular edema, cystoid macular edema, lattice degeneration, macular disease, macular degeneration, hereditary macular dystrophy, macular edema, macular hole, macular pucker, central serous chorioretinopathy, ocular histoplasmosis syndrome (OHS), posterior vitreous detachment, retinal detachment, retinal artery obstruction, retinal vein occlusion, retinoblastoma, retinopathy of prematurity (ROP), retinitis pigmentosa, acquired or x-linked retinoschisis, stargardt's disease, toxoplasmosis of retina and uveitis.

* * * * *